United States Patent
Nessim et al.

(10) Patent No.: US 11,893,734 B1
(45) Date of Patent: Feb. 6, 2024

(54) SYSTEM AND METHOD FOR AN ARTIFICIAL INTELLIGENCE DRIVEN IMAGE ACQUISITION SYSTEM

(71) Applicants: Maurice Nessim, Houston, TX (US); Yi Luo, Houston, TX (US); Yanwei Xue, Houston, TX (US); Chuck Peng, Houston, TX (US)

(72) Inventors: Maurice Nessim, Houston, TX (US); Yi Luo, Houston, TX (US); Yanwei Xue, Houston, TX (US); Chuck Peng, Houston, TX (US)

(*) Notice: Subject to any disclaimer, the term of this patent is extended or adjusted under 35 U.S.C. 154(b) by 0 days.

(21) Appl. No.: 17/993,699

(22) Filed: Nov. 23, 2022

(51) Int. Cl.
| | |
|---|---|
| *G06T 7/00* | (2017.01) |
| *G06N 5/022* | (2023.01) |
| *G16H 30/20* | (2018.01) |
| *A61B 5/06* | (2006.01) |

(52) U.S. Cl.
CPC .......... *G06T 7/0012* (2013.01); *A61B 5/065* (2013.01); *G06N 5/022* (2013.01); *G16H 30/20* (2018.01); *G06T 2207/10132* (2013.01); *G06T 2207/10136* (2013.01)

(58) Field of Classification Search
None
See application file for complete search history.

(56) References Cited

U.S. PATENT DOCUMENTS 6,969,354 B1 * 11/2005 Marian ................ A61B 8/4488
600/439

2016/0058420 A1 * 3/2016 Cinthio ................ A61B 8/54
600/458
2021/0407648 A1 * 12/2021 Ravishankar .......... G16H 50/20

OTHER PUBLICATIONS

Li, Keyu, et al. "Autonomous navigation of an ultrasound probe towards standard scan planes with deep reinforcement learning." 2021 IEEE International Conference on Robotics and Automation (ICRA). IEEE, 2021. (Year: 2021).*
Droste, Richard, et al. "Automatic probe movement guidance for freehand obstetric ultrasound." Medical Image Computing and Computer Assisted Intervention—MICCAI 2020: 23rd International Conference, Lima, Peru, Oct. 4-8, 2020, Proceedings, Part III 23. Springer International Publishing, 2020. (Year: 2020).*
Chatelain, Pierre, Alexandre Krupa, and Nassir Navab. "Optimization of ultrasound image quality via visual servoing." 2015 IEEE international conference on robotics and automation (ICRA). IEEE, 2015. (Year: 2015).*
Deng, Xutian, et al. "Learning robotic ultrasound scanning skills via human demonstrations and guided explorations." 2021 IEEE International Conference on Robotics and Biomimetics (ROBIO). IEEE, 2021. (Year: 2021).*

* cited by examiner

*Primary Examiner* — Samah A Beg
(74) *Attorney, Agent, or Firm* — Hunton Andrews Kurth LLP (57) ABSTRACT

The present embodiments relate generally to a probe, system, and method for generating a predictive model for moving the probe. The probe can include a movable element that move according to the suggestion of the predictive model. The system can include the probe, a user device, an administrator processor, and a server. The predictive model calculates an image score based on the quality, then the processor can move the movable element based on the score.

20 Claims, 8 Drawing Sheets

SYSTEM AND METHOD FOR AN ARTIFICIAL INTELLIGENCE DRIVEN IMAGE ACQUISITION SYSTEM

FIELD OF DISCLOSURE

The present disclosure relates to a probe, system, and method for generating an artificial intelligence model that prompts the probe's movable element to generate a better image.

BACKGROUND

Ultrasound probes are used in the medical imaging industry to generate multi-dimensional images of patients or objects. These probes emit sound waves into the patient then receive the reflected waves, thus generating an image. Conventional probes have a handle attached to scanner that is applied directly to the patient or object. For example, an ultrasound probe can be placed on a patient's lower stomach to generate an image of the patient's uterus. To make an image that is clear and comprehensive, the probe must be moved around to many locations and in many directions against the patient. This is because human organs are 3D objects, while current ultrasound probes can only make 2D images or it only illuminate a small zones/slice of a large 3D organ. The situation is like one hold a flashlight entering in a dark room, one must keep rotating the directions of the flashlight according to what one can see currently until we find the desired object (say a piano). In addition, because conventional ultrasound probes are controlled entirely by the hands of the health professional administering the procedure, human error can occur (i.e., one may overlook the piano). Due to the 2D limitation of the probes and possible human ignorance, the conventional ultrasound probes can often be time-consuming, inaccurate, and frustrating for both the health professional and the patient.

These and other deficiencies exist. Therefore, there is a need to provide an ultrasound probe that overcomes these deficiencies.

SUMMARY OF THE DISCLOSURE

Aspects of the disclosed embodiments include a probe, system, and method for generating an artificial intelligence model for moving a moveable element of the probe in a direction most helpful for creating a clear ultrasound image of a specifically wanted portion (e.g., the mitral) in a targeted organ (e.g., heart).

Embodiments of the present disclosure include a probe with a movable element connecting a lens (or transducers) and a handle, the probe comprising: a body, wherein the body further comprises: a handle; a lens; and a movable element. The movable element can connect the handle and the lens. The movable element is configured to move the lens in response to one or more commands from a predetermined algorithm configured to determine the optimal movement of the lens in relation to a clear image of an object.

Embodiments of the present disclosure also include a system configured to acquire improved ultrasound images, the system comprising: a probe, which further comprises a body, wherein the body further comprises: a handle; a lens; and a movable element. The movable element connects the handle and the lens. The movable element is configured to move the lens in response to one or more commands from a predetermined algorithm configured to determine the optimal movement of the lens in relation to a clear image of an object. The system further includes a processor configured to move the movable element of the probe, wherein the processor is further configured to: receive, from the probe, one or more images; analyze, upon receiving the images, the images for quality; generate, upon analyzing the images for quality, a predictive model configured to determine an image score based on the quality of the images wherein the predictive model comprises a model of image quality versus the location of the probe with respect to the subject; calculate, by the predictive model, the image score for one or more images; and move, upon calculating the image score, the movable element of the probe.

Embodiments of the present disclosure also include a method for applying a probe guided by a predetermined algorithm, the method comprising the steps of: receiving, by a processor from a probe, one or more images. Next, the method proceeds with analyzing, by the processor upon receiving the images, the images for quality. Then, the method proceeds with generating, by the processor upon analyzing the images for quality, a predictive model configured to determine an image score based on the quality of the images wherein the predictive model comprises a model of image quality versus the location of the probe with respect to the object. Next, the method proceeds with calculating, by the predictive model, the image score for the one or more images; and moving, by the processor upon calculating the image score, the movable element of the probe.

BRIEF DESCRIPTION OF THE DRAWINGS

In order to facilitate a fuller understanding of the present invention, reference is now made to the attached drawings. The drawings should not be construed as limiting the present invention, but are intended only to illustrate different aspects and embodiments of the invention.

DETAILED DESCRIPTION

Exemplary embodiments of the invention will now be described in order to illustrate various features of the invention. The embodiments described herein are not intended to be limiting as to the scope of the invention, but rather are intended to provide examples of the components, use, and operation of the invention.

Furthermore, the described features, advantages, and characteristics of the embodiments may be combined in any suitable manner. One skilled in the relevant art will recognize that the embodiments may be practiced without one or more of the specific features or advantages of an embodiment. In other instances, additional features and advantages may be recognized in certain embodiments that may not be present in all embodiments.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Generally, the following embodiments disclose a probe with a movable element that can be controlled or commanded by a predictive model, neural network, or some artificial intelligence. The probe can be an ultrasound probe, but it is understood that other probes that capture, create, or otherwise generate images can be used. The probe can include a handle, a lens, and a movable element connecting the handle and the lens. The handle can be a handle that is conducive to being held by human hands or a robotic arm. The handle can be composed of any suitable material, including without limitation plastic or metal. The handle can include within its housing one or more motors and one or more motor controllers, as well as any necessary circuitry. These motors and circuitry are responsible for moving the movable element. The moveable element can include one or more robotic joints which allow the moveable element to move on any number of linear and rotational axes. The moveable element attaches the end of the handle to the lens such that the lens can move independent of the handle. The moveable element can be moved by a processor associated with a predictive model, neural network, or artificial intelligence designed to figure out the best, optimal, most efficient, or quickest path towards generating an ultrasound image of sufficient quality. The predictive model can, over a predetermined number of iterations, learn the best way to produce an image based on the movements and positions of the probe. When the probe is being used on an object or patient, the predictive model can give an image score for every image being captured or generated by the probe. The image score is a grade of quality given to the image that reflects the quality of the image. The quality of the image can be based on a number of factors, including without limitation the clarity, depth, angle, dimension, and accuracy of the one or more images. The quality can also be based on other factors such as the procedure being performed, the party of the body being scanned or probed, a patient's history, and other historical data concerning the quality of ultrasound images. Having learned from all these factors, the predictive element can generate an image score of the one or more images generated by the probe. Based on the image score, the predictive model can calculate a movement command or movement suggestion for the probe. The movement command or movement suggestion can be sent to one or more processors associated with the probe or an administrator processor. The processors process the movement command and move the movable element accordingly. Thus, the lens is moved in a direction or angle that will achieve a higher image quality.

By combining artificial intelligence and a robotic appendage via a movable element, users of ultrasound probes can produce better images. For example, a health administrator may be taking an ultrasound of a uterus. Rather than check and re-check a user display for the corresponding images, the user can rely on the movable element to tell them where to move the probe next. This reduces human error; makes ultrasound procedures faster and easier; reduces the amount of training needed to use an ultrasound probe; reduces patient frustration; and ultimately results in saving time, money, and effort. Thus, the disclosed embodiments provide an improvement on conventional ultrasound probes, conventional ultrasound procedures, and conventional calculations of ultrasound image quality. The combination of the movable element and the predictive model provides an intuitive and helpful improvement to ultrasound technology. Furthermore, the addition of cloud servers, cloud systems, cloud processors, and cloud technology can greatly improve the speed with which the images and image scores are generated.

Figure 1:
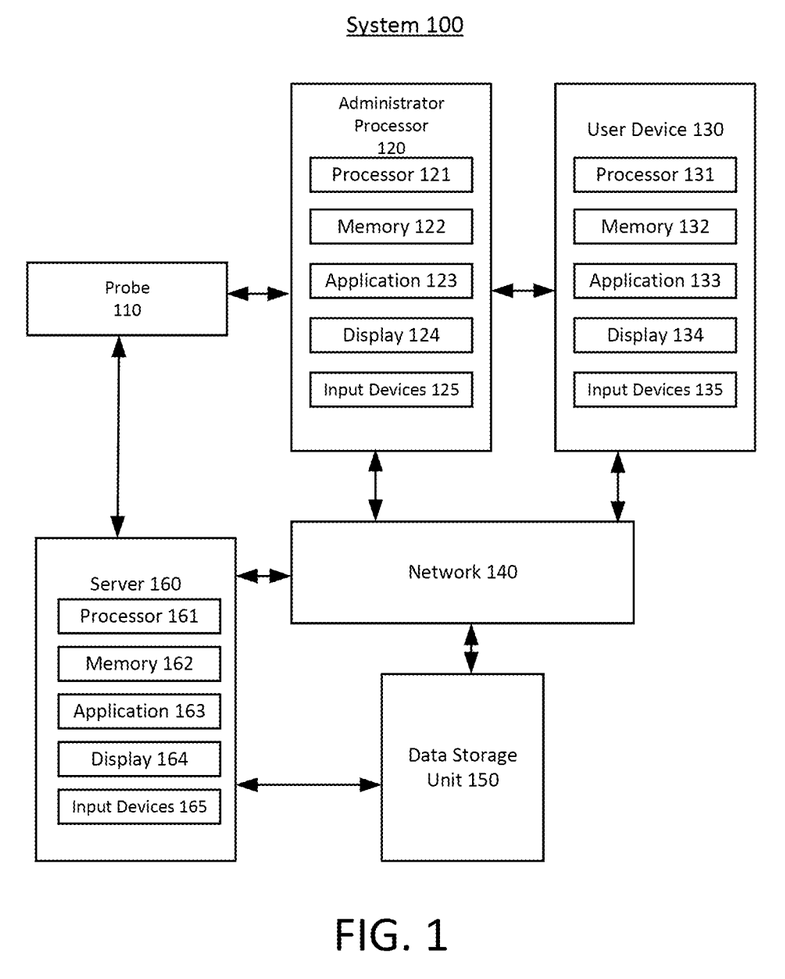
FIG. 1 illustrates a system according to an exemplary embodiment.

FIG. 1 illustrates a system according to an exemplary embodiment. The system can include a probe, an administrator processor, a user device, a network, a data storage unit, and a server.

The system can include one or more probes 110. Probes 110 are discussed with further reference to FIGS. 2, 3, and 4.

The system can include one or more administrator processors 120. The administrator processors 120 may include a processor 121, a memory 122, and an application 123. The processor 121 may be a processor, a microprocessor, or other processor, and the administrator processors 120 may include one or more of these processors. The processor 121 may include processing circuitry, which may contain additional components, including additional processors, memories, error and parity/CRC checkers, data encoders, anti-collision algorithms, controllers, command decoders, security primitives and tamper-proofing hardware, as necessary to perform the functions described herein.

The processor 121 may be coupled to the memory 122. The memory 122 may be a read-only memory, write-once read-multiple memory or read/write memory, e.g., RAM, ROM, and EEPROM, and the administrator processors 120 may include one or more of these memories. A read-only memory may be factory programmable as read-only or one-time programmable. One-time programmability provides the opportunity to write once then read many times. A write-once read-multiple memory may be programmed at one point in time. Once the memory is programmed, it may not be rewritten, but it may be read many times. A read/write memory may be programmed and re-programed many times after leaving the factory. It may also be read many times. The memory 122 may be configured to store one or more software applications, such as the application 123, and other data, such as user's private data and financial account information.

The application 123 may comprise one or more software applications, such as a mobile application and a web browser, comprising instructions for execution on the administrator processor 120. In some examples, the administrator processor 120 may execute one or more applications, such as software applications, that enable, for example, network communications with one or more components of the system 100, transmit and/or receive data, and perform the functions described herein. Upon execution by the processor 121, the application 123 may provide the functions described in this specification, specifically to execute and perform the steps and functions in the process flows described below. Such processes may be implemented in software, such as software modules, for execution by computers or other machines. The application 123 may provide graphical user interfaces (GUIs) through which a user may view and interact with other components and devices within the system 100. The GUIs may be formatted, for example, as web pages in HyperText Markup Language (HTML), Extensible Markup Language (XML) or in any other suitable form for presentation on a display device depending upon applications used by users to interact with the system 100.

The administrator processor 120 may further include a display 124 and input devices 125. The display 124 may be any type of device for presenting visual information such as a computer monitor, a flat panel display, and a mobile device screen, including liquid crystal displays, light-emitting diode displays, plasma panels, and cathode ray tube displays. The input devices 125 may include any device for entering information into the administrator processor 120 that is available and supported by the administrator processor 120, such as a touch-screen, keyboard, mouse, cursor-control device, touch-screen, microphone, digital camera, video recorder or camcorder. These devices may be used to enter information and interact with the software and other devices described herein. The administrator processor can be connected to the probe 110 via a wired or wireless connection.

The system can include one or more user devices 130. The user device 130 may be a network-enabled computer device. Exemplary network-enabled computer devices include, without limitation, a server, a network appliance, a personal computer, a workstation, a phone, a handheld personal computer, a personal digital assistant, a thin client, a fat client, an Internet browser, a mobile device, a kiosk, or other a computer device or communications device. For example, network-enabled computer devices may include an iPhone, iPod, iPad from Apple® or any other mobile device running Apple's iOS® operating system, any device running Microsoft's Windows® Mobile operating system, any device running Google's Android® operating system, and/or any other smartphone, tablet, or like wearable mobile device.

The user device 130 may include a processor 131, a memory 132, and an application 133. The processor 131 may be a processor, a microprocessor, or other processor, and the user device 130 may include one or more of these processors. The processor 131 may include processing circuitry, which may contain additional components, including additional processors, memories, error and parity/CRC checkers, data encoders, anti-collision algorithms, controllers, command decoders, security primitives and tamper-proofing hardware, as necessary to perform the functions described herein.

The processor 131 may be coupled to the memory 132. The memory 132 may be a read-only memory, write-once read-multiple memory or read/write memory, e.g., RAM, ROM, and EEPROM, and the user device 130 may include one or more of these memories. A read-only memory may be factory programmable as read-only or one-time programmable. One-time programmability provides the opportunity to write once then read many times. A write-once read-multiple memory may be programmed at one point in time. Once the memory is programmed, it may not be rewritten, but it may be read many times. A read/write memory may be programmed and re-programed many times after leaving the factory. It may also be read many times. The memory 132 may be configured to store one or more software applications, such as the application 133, and other data, such as user's private data and financial account information.

The application 133 may comprise one or more software applications, such as a mobile application and a web browser, comprising instructions for execution on the user device 130. In some examples, the user device 130 may execute one or more applications, such as software applications, that enable, for example, network communications with one or more components of the system 100, transmit and/or receive data, and perform the functions described herein. Upon execution by the processor 131, the application 133 may provide the functions described in this specification, specifically to execute and perform the steps and functions in the process flows described below. Such processes may be implemented in software, such as software modules, for execution by computers or other machines. The application 133 may provide graphical user interfaces (GUIs) through which a user may view and interact with other components and devices within the system 100. The GUIs may be formatted, for example, as web pages in HyperText Markup Language (HTML), Extensible Markup Language (XML) or in any other suitable form for presentation on a display device depending upon applications used by users to interact with the system 100.

The user device 130 may further include a display 134 and input devices 135. The display 134 may be any type of device for presenting visual information such as a computer monitor, a flat panel display, and a mobile device screen, including liquid crystal displays, light-emitting diode displays, plasma panels, and cathode ray tube displays. The input devices 135 may include any device for entering information into the user device 130 that is available and supported by the user device 130, such as a touch-screen, keyboard, mouse, cursor-control device, touch-screen, microphone, digital camera, video recorder or camcorder. These devices may be used to enter information and interact with the software and other devices described herein. The user device can be connected via a wireless or wired connection with the administrator processor 120, server 160, and probe 110.

System 100 may include one or more networks 140. In some examples, the network 140 may be one or more of a wireless networks, a wired network or any combination of wireless network and wired network, and may be configured to connect the user device 130, the server 160, the data storage unit 150 and the server 160. For example, the network 140 may include one or more of a fiber optics network, a passive optical network, a cable network, an Internet network, a satellite network, a wireless local area network (LAN), a Global System for Mobile Communication, a Personal Communication Service, a Personal Area Network, Wireless Application Protocol, Multimedia Messaging Service, Enhanced Messaging Service, Short Message Service, Time Division Multiplexing based systems, Code Division Multiple Access based systems, D-AMPS, Wi-Fi, Fixed Wireless Data, IEEE 802.11b, 802.15.1, 802.11n and 802.11g, Bluetooth, NFC, Radio Frequency Identification (RFID), Wi-Fi, and/or the like.

In addition, the network 140 may include, without limitation, telephone lines, fiber optics, IEEE Ethernet 902.3, a wide area network, a wireless personal area network, a LAN, or a global network such as the Internet. In addition, the network 140 may support an Internet network, a wireless communication network, a cellular network, or the like, or any combination thereof. The network 140 may further include one network, or any number of the exemplary types of networks mentioned above, operating as a stand-alone network or in cooperation with each other. The network 140 may utilize one or more protocols of one or more network elements to which they are communicatively coupled. The network 140 may translate to or from other protocols to one or more protocols of network devices. Although the network 140 is depicted as a single network, it should be appreciated that according to one or more examples, the network 140 may comprise a plurality of interconnected networks, such as, for example, the Internet, a service provider's network, a cable television network, corporate networks, such as credit card association networks, and home networks. The network 140 may further comprise, or be configured to create, one or more front channels, which may be publicly accessible and through which communications may be observable, and one or more secured back channels, which may not be publicly accessible and through which communications may not be observable.

System 100 may include a database or data storage unit 150. The data storage unit 150 may be one or more databases configured to store data, including without limitation, private data of users, financial accounts of users, identities of users, transactions of users, and certified and uncertified documents. The database 150 may comprise a relational database, a non-relational database, or other database implementations, and any combination thereof, including a plurality of relational databases and non-relational databases. In some examples, the database 150 may comprise a desktop database, a mobile database, or an in-memory database. Further, the database 150 may be hosted internally by the server 130 or may be hosted externally of the server 160, such as by a server, by a cloud-based platform, or in any storage device that is in data communication with the server 160. The data storage unit can be independent of the memory elements described elsewhere in FIG. 1. The data storage unit can be configured for long term storage or storage for later use.

The system can include a server 160. The server 160 may be a network-enabled computer device. Exemplary network-enabled computer devices include, without limitation, a server, a network appliance, a personal computer, a workstation, a phone, a handheld personal computer, a personal digital assistant, a thin client, a fat client, an Internet browser, a mobile device, a kiosk, a contactless card, or other a computer device or communications device. For example, network-enabled computer devices may include an iPhone, iPod, iPad from Apple® or any other mobile device running Apple's iOS® operating system, any device running Microsoft's Windows® Mobile operating system, any device running Google's Android® operating system, and/or any other smartphone, tablet, or like wearable mobile device. The server may be a combination of one or more cloud computing systems including without limitation public clouds, private clouds, hybrid clouds, multi-clouds, and high-performance clouds.

The server 160 may include a processor 161, a memory 162, and an application 163. The processor 161 may be a processor, a microprocessor, or other processor, and the server 160 may include one or more of these processors. The processor 161 may include processing circuitry, which may contain additional components, including additional processors, memories, error and parity/CRC checkers, data encoders, anti-collision algorithms, controllers, command decoders, security primitives and tamper-proofing hardware, as necessary to perform the functions described herein.

The processor 161 may be coupled to the memory 162. The memory 162 may be a read-only memory, write-once read-multiple memory or read/write memory, e.g., RAM, ROM, and EEPROM, and the server 160 may include one or more of these memories. A read-only memory may be factory programmable as read-only or one-time programmable. One-time programmability provides the opportunity to write once then read many times. A write-once read-multiple memory may be programmed at one point in time. Once the memory is programmed, it may not be rewritten, but it may be read many times. A read/write memory may be programmed and re-programed many times after leaving the factory. It may also be read many times. The memory 162 may be configured to store one or more software applications, such as the application 163, and other data, such as user's private data and financial account information.

The application 163 may comprise one or more software applications, such as a mobile application and a web browser, comprising instructions for execution on the server 160. In some examples, the server 160 may execute one or more applications, such as software applications, that enable, for example, network communications with one or more components of the system 100, transmit and/or receive data, and perform the functions described herein. Upon execution by the processor 161, the application 163 may provide the functions described in this specification, specifically to execute and perform the steps and functions in the process flows described below. Such processes may be implemented in software, such as software modules, for execution by computers or other machines. The application 163 may provide graphical user interfaces (GUIs) through which a user may view and interact with other components and devices within the system 100. The GUIs may be formatted, for example, as web pages in HyperText Markup Language (HTML), Extensible Markup Language (XML) or in any other suitable form for presentation on a display device depending upon applications used by users to interact with the system 100.

The server 160 may further include a display 164 and input devices 165. The display 164 may be any type of device for presenting visual information such as a computer monitor, a flat panel display, and a mobile device screen, including liquid crystal displays, light-emitting diode displays, plasma panels, and cathode ray tube displays. The input devices 165 may include any device for entering information into the server 160 that is available and supported by the server 160, such as a touch-screen, keyboard, mouse, cursor-control device, touch-screen, microphone, digital camera, video recorder or camcorder. These devices may be used to enter information and interact with the software and other devices described herein.

Figure 2:
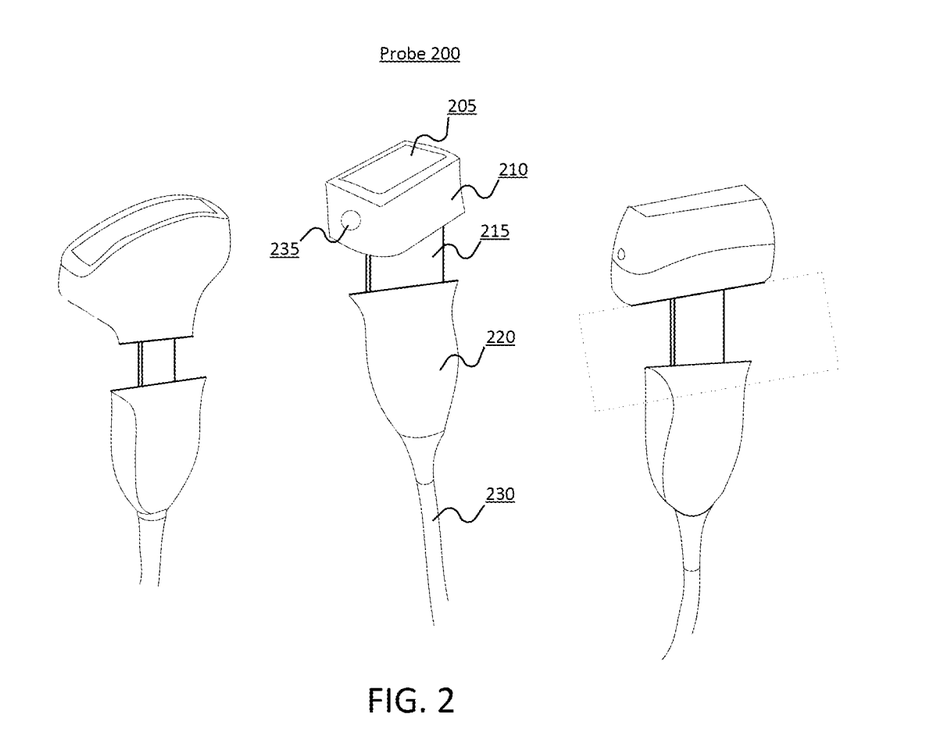
FIG. 2 is a diagram illustrating probes with movable elements according to an exemplary embodiment.

FIG. 2 is a diagram of a probe with a movable element according to an exemplary embodiment. Generally, the probe can be an ultrasound probe, although it is understood that other probes capable of producing images from sound waves can be used. In some embodiments, the probe can be applied to a human patient or human subject. In other embodiments, the probe can be applied to a different living organism. In still other embodiments, the probe can be applied to an inanimate object. The ultrasound probe can include one or more ultrasound transducers. The transducers can contain piezoelectric crystals capable of producing sound waves. The probe can be scanned on the longitudinal plane or the transverse plane with respect to the object or patient, or any direction or angle suitable for generating sufficient images of the object. The probe can generate a sagittal plane image, or a coronal plane image (x and y axis). The probe can have three degrees of movement along the x, y and z axes, and it has three degrees of rotational movement to achieve roll, pitch, yaw. The probe can include without limitation a linear probe (used for procedures, only 6 cm deep but high resolution; good for finding veins); a curvilinear probe (used for abdominal exams, much deeper field; low frequency, up to 30 cm into the body; or a phased array probe (used for cardiac exams). Other probe types or lens types can include without limitation micro convex, T-type linear, biplanar, endocavitary, and intrarectal. It is understood that the movable element is not limited to any kind of probe, and other probes not listed herein are considered.

The probe 200 can have a lens 205 configured to be pressed against the patient or object. The lens 205 can be located at the upper extremity of the housing 210. The lens 205 can generally emit the sound waves from the probe, onto the patient or object, and back onto the probe 205, thus creating one or more images. Connecting the housing 210 to the handle 220 is the movable element 215. The movable element 215 is discussed with further reference to FIG. 4. Generally, the movable element 215 can move the housing 210 and by association the lens 205. The handle 220 can be generally configured to be held firmly by a human hand or robotic arm such that the lens 205 can move while the handle 220 remains still. The handle 220 can generally include one or more motor controls and one or more motors that control the movable element 215. The motor controls are discussed with further reference to FIG. 4. At the lower extremity of the handle 220 is the wire 230 that can connect the probe to a power source, one or more processors or administrator processors, one or more user devices, and one or more servers. On the housing 210 can be one or more dynamic element 235 that can emit light in response to the movement of the probe. The responsiveness of the probe is discussed with further reference to FIG. 8.

Figure 3:
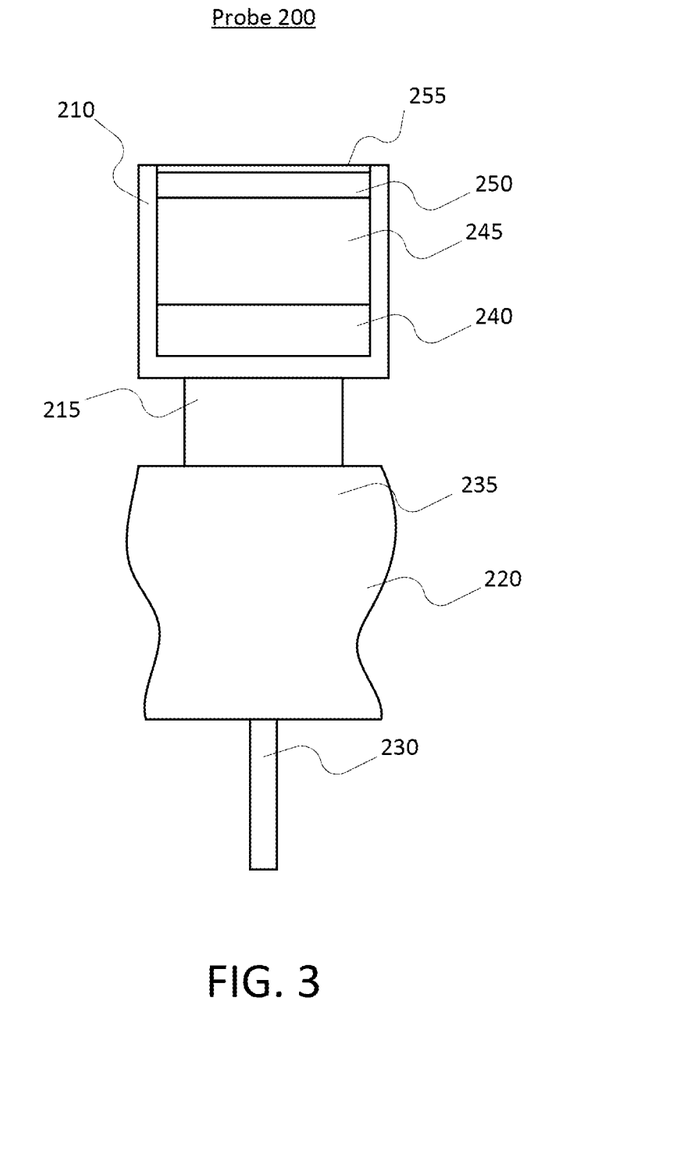
FIG. 3 is a cross sectional perspective of a probe with a movable element according to an exemplary embodiment.

FIG. 3 is a cross-sectional diagram of a probe with a movable element according to an exemplary embodiment. The probe is discussed further with reference to FIG. 2 and FIG. 4.

The probe end 210 is connected to the handle 220 by the movable element 215. The probe end 210 can include a matching layer 255, an acoustic layer 250, a piezoelectric crystal or piezoelectric material 245, and a backing material 240. The probe end 210 as depicted in FIG. 3 is a linear array probe. In other embodiments, the probe can be a convex array, linear array, phased array, micro convex array, T-type array, biplanar array, endocavitary array, and intrarectal array. At an extremity of the probe end 210 is the matching layer 255 that can be the interface between the probe end 210 and the tissue of the patient. The acoustic layer 250 can amplify the sound waves. The piezoelectric material 245 can generate, upon being affected by an electric current, ultrasound waves that hit the tissue of the patient, then bounce back to the probe 210. The backing material 240 can be placed behind the piezoelectric material 245 to shorten the pulse of the piezoelectric materials, thus creating a better image. Though FIG. 3 illustrates these components in a single order, it is understood that these elements do not necessarily have to be positioned as shown. Other elements known in the art can be included. A wire or connection 230 can connect the probe to a power source and/or the administrator processor, user device, server, data storage unit, or power source.

Figure 4:
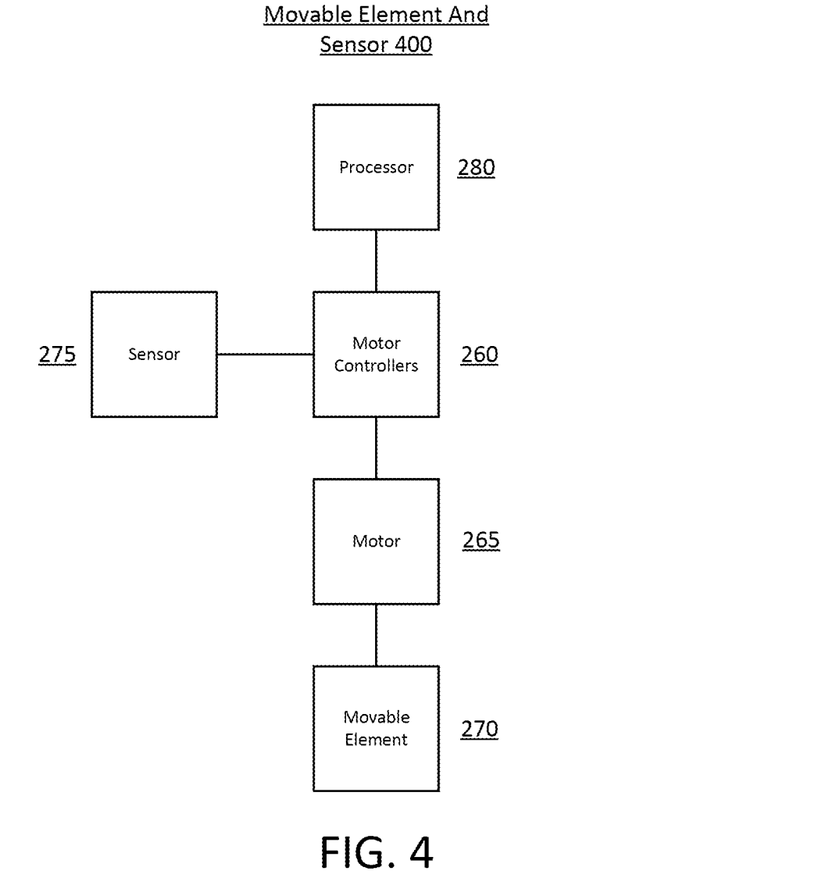
FIG. 4 is diagram of a probe with a movable element according to an exemplary embodiment.

FIG. 4 is a block diagram of the movable element according to an exemplary embodiment. Generally, the movable element 270 can connect the handle of the probe to the scanner, lens, or matching layer at the extremity of the probe.

The probe 110 a may include a robot control module for controlling the operation, and the robot control module may refer to a software module or a chip implementing the software module by hardware. The probe can be connected via a wired connection to the administrator processor 120. The administrator processor 120 is discussed with further reference to FIG. 1.

The operation of the movable element is controlled by signals from a processor 280, including without limitation a microprocessor, microcontroller, application-specific integrated circuit, filed programmable gate array, or other logic circuitry. The processor 280 can be physically located within the probe or it can be a part of a computer-enable device connected to the probe such as the administrator processor 120. The probe can itself have a processor. In other embodiments, the processor can instead be associated with an administrator processor, user device, server, or some other processors separate from the probe. The probe can be connected to a power source so that it may power the processor. The processor 280 can be communicatively linked to one or more motor controllers 260 and motors 265 for the joints of the movable element 270. The processor and the motor controllers can communicate with each other over one or more buses using a proprietary protocol or a standard protocol. The housing of the probe may include a sensor 275 that measure linear force and/or torque based on the torque experience at the motor and send a corresponding signal back to the processor reporting the measurement.

Figure 5:
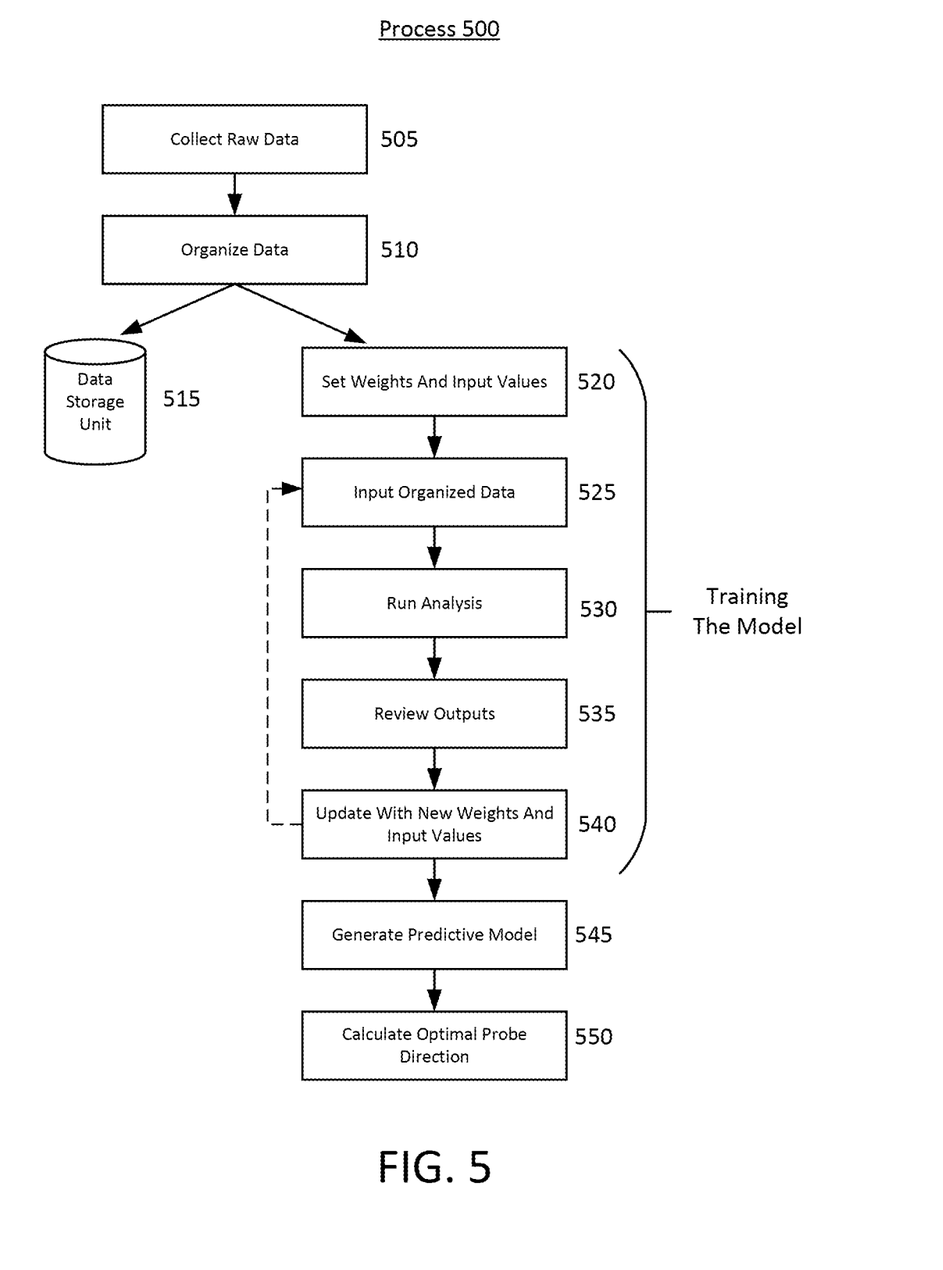
FIG. 5 is a flowchart of generating a predictive model according to an exemplary embodiment.

FIG. 5 is a flowchart describing the generation of the predictive model according to an exemplary embodiment.

The process 500 describes the training process for an exemplary predictive model, neural network, or artificial intelligence suitable for calculating an image score and predicting the next best movement for the probe and/or the movable element. The process can begin with action 505 when raw data is collected. The raw data can be associated with the probe location, probe angle, probe movement, patient, type of probe, type of procedure, patient history, part of the body being scanned, or other information. The collection of raw data can be performed by a processor or application associated with the user device or server. The raw data can be transmitted over a wired or wireless network. The data may have been previously gathered and stored in a database or data storage unit in which case the processor or application can retrieve the data from the data storage unit. The data storage unit can be configured to store the data for long term usage or later usage by the predictive model, the administrator processor, or user device. At action 510, the processor or application can organize the raw data into discernable categories including but not limited to probe location and probe angle. These categories may be adjusted by the user or the predictive model according to the needs of the model. The categories themselves can be predetermined by the user or created by the predictive model. At action 515, the organized or raw data can be transmitted to the data storage unit. The data storage unit can be associated with the user device, the administrator processor, or server. The raw or organized data can be transmitted over a wired network, wireless network, or one or more express buses. Upon organizing the data into one or categories, the processor or application can proceed with training the predictive model in actions 520 through 540. Generally, the training portion can have any number of iterations. The predictive model can comprise one or more neural network described with further reference to FIG. 6.

The training portion can begin with action 520 when the weights and input values are set by the user or by the model itself. Furthermore, the weights can be the predetermined connections between the inputs and the hidden layers described with further reference to FIG. 6. The input values are the values that are fed into the neural network. The input values may be discerned by the different categories created in action 510, although other distinct input values may be discerned. In action 525, the data in inputted in the neural network, and in action 530 the neural network analyzes the data according to the weights and other parameters set by the user. In action 535, the outputs are reviewed. The outputs can include one or more image scores, movement suggestions, or movement commands suitable to be sent to the probe, the user device, or the administrator processor. In action 540, the predictive model may be updated with new data and parameters. The new data can be collected by the processor in a similar fashion to actions 505 and 510. Though it is not necessary in this exemplary embodiment to retrain the predictive model, the predictive model can be re-trained any number times such that actions 525 through 540 are repeated until a satisfactory output is achieved or some other parameter has been met. As another nonlimiting example, the user can adjust the weighted relationship between the input layer and the one or more hidden layers of a neural network discussed with further reference to FIG. 6. If a satisfactory output has been recorded, then in action 545 one or more predictive models can be generated. It is understood that the predictive model, once generated, can undergo further training similar to actions 520 to 545. Having generated the predictive model, in action 550 the model can calculate an image score given the unique input values collected from the user.

Figure 6:
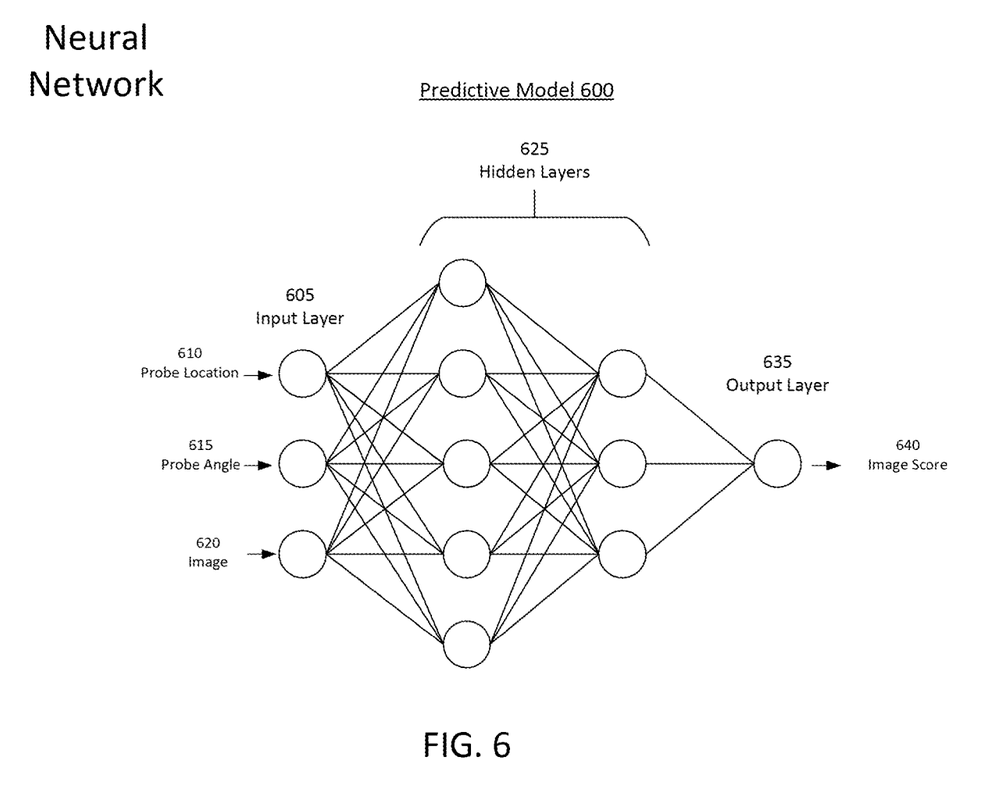
FIG. 6 is a diagram of a neural network according to an exemplary embodiment.

FIG. 6 is a flowchart illustrating a neural network according to an exemplary embodiment. The neural network can be associated with the predictive model. That is, the neural network can be implemented to create the predictive model, but the neural network can be the predictive model itself as well.

A neural network is a series of algorithms that can, under predetermined training restrictions, recognize relationships between one or more variables. A neuron in a neural network is a mathematical function that collects and classifies information according to a specific form set by a user. Generally, a neural network can be divided into three main components: an input layer, a processing or hidden layer, and an output layer. The input layer comprises data sets chosen to be inserted into the neural network for analysis. The hidden layers include one or more neurons that can classify the inputs according to parameters set by the user. The hidden layers can comprise multiple successive layers, the first layer positioned immediately after the input layer and the last layer positioned immediately before the output layer. The hidden layer immediately after the input layer may be connected to the input layer via a predetermined weight or emphasis. These weights can be assigned according to the modeler's agenda. Alternatively, the model itself can determine the optimal weights between layers such that a predetermined outcome, margin of error, or minimum data point is achieved.

The predictive model can comprise a neural network 600. The neural network may be integrated into the server, the user device, the administrator processor, or some other computer device suitable for neural network analysis. The neural network can include generally an input layer 605, one or more hidden layers 625, and an output layer 635. Although only a certain number of nodes are depicted in FIG. 6, it is understood that the neural network according to the disclosed embodiments may include less or more nodes in each layer. Additionally, the hidden layers can include more or less layers than what is depicted in FIG. 6. It is also understood that the connections between each layer may be assigned a predetermined weight according to user's manual change or according to some weight value generated by the neural network itself. The input layer may include sets of data gathered from the probe, the data storage unit, or some outside source The neural network can include probe and image information including probe location 610, probe angle 615, and one or more images 620. Other inputs not depicted in FIG. 6 may also be considered such as the concavity of the lens or matching layer, the part of the body being scanned, the type of tissue being scanned, time spent scanning a particular area, type of ultrasound procedure being performed, or other information. The neurons associated with the hidden layers can be trained or provisioned to classify the inputs according to parameters set by the user. As a nonlimiting example, the user can train the hidden layer to associate an ultrasound procedure of a uterus with one or more suitable angles. As another example, the hidden layer can be trained to associate a certain body location—for example, the chest area—with a specific scanning pattern, for example a circle pattern. Upon analyzing the inputs via the one or more hidden layers, the neural network can create an image score 640. It is understood that one or more neural networks or some combination of neural networks can be trained according to an individual probe, procedure, patient, object, body part, or some combination therein. The exemplary system, method, and computer-readable medium can then apply the generated models to calculate a most efficient movement of the movable element or the entire probe itself.

The predictive models described herein can utilize a Bidirectional Encoder Representations from Transformers (BERT) models. BERT models utilize use multiple layers of so called "attention mechanisms" to process textual data and make predictions. These attention mechanisms effectively allow the BERT model to learn and assign more importance to words, images, or actions that are more important in making whatever inference is trying to be made.

The exemplary system, method and computer-readable medium can utilize various neural networks, such as convolutional neural networks (CNNs) or recurrent neural networks (RNNs), to generate the exemplary models. A CNN can include one or more convolutional layers (e.g., often with a subsampling step) and then followed by one or more fully connected layers as in a standard multilayer neural network. CNNs can utilize local connections and can have tied weights followed by some form of pooling which can result in translation invariant features.

A RNN is a class of artificial neural network where connections between nodes form a directed graph along a sequence. This facilitates the determination of temporal dynamic behavior for a time sequence. Unlike feedforward neural networks, RNNs can use their internal state (e.g., memory) to process sequences of inputs. A RNN can generally refer to two broad classes of networks with a similar general structure, where one is finite impulse, and the other is infinite impulse. Both classes of networks exhibit temporal dynamic behavior. A finite impulse recurrent network can be or can include a directed acyclic graph that can be unrolled and replaced with a strictly feedforward neural network, while an infinite impulse recurrent network can be, or can include, a directed cyclic graph that may not be unrolled. Both finite impulse and infinite impulse recurrent networks can have additional stored state, and the storage can be under the direct control of the neural network. The storage can also be replaced by another network or graph, which can incorporate time delays or can have feedback loops. Such controlled states can be referred to as gated state or gated memory and can be part of long short-term memory networks (LSTMs) and gated recurrent units.

RNNs can be similar to a network of neuron-like nodes organized into successive "layers," each node in a given layer being connected with a directed e.g., (one-way) connection to every other node in the next successive layer. Each node (e.g., neuron) can have a time-varying real-valued activation. Each connection (e.g., synapse) can have a modifiable real-valued weight. Nodes can either be (i) input nodes (e.g., receiving data from outside the network), (ii) output nodes (e.g., yielding results), or (iii) hidden nodes (e.g., that can modify the data en route from input to output). RNNs can accept an input vector x and give an output vector y. However, the output vectors are based not only by the input just provided in, but also on the entire history of inputs that have been provided in in the past.

For supervised learning in discrete time settings, sequences of real-valued input vectors can arrive at the input nodes, one vector at a time. At any given time step, each non-input unit can compute its current activation (e.g., result) as a nonlinear function of the weighted sum of the activations of all units that connect to it. Supervisor-given target activations can be supplied for some output units at certain time steps. For example, if the input sequence is a speech signal corresponding to a spoken digit, the final target output at the end of the sequence can be a label classifying the digit. In reinforcement learning settings, no teacher provides target signals. Instead, a fitness function, or reward function, can be used to evaluate the RNNs performance, which can influence its input stream through output units connected to actuators that can affect the environment. Each sequence can produce an error as the sum of the deviations of all target signals from the corresponding activations computed by the network. For a training set of numerous sequences, the total error can be the sum of the errors of all individual sequences.

The models described herein may be trained on one or more training datasets, each of which may comprise one or more types of data. In some examples, the training datasets may comprise previously collected data, such as data collected from previous uses of the same type of systems described herein and data collected from different types of systems. In other examples, the training datasets may comprise continuously collected data based on the current operation of the instant system and continuously collected data from the operation of other systems. In some examples, the training dataset may include anticipated data, such as the anticipated future workloads, currently scheduled workloads, and planned future workloads, for the instant system and/or other systems. In other examples, the training datasets can include previous predictions for the instant system and other types of system and may further include results data indicative of the accuracy of the previous predictions. In accordance with these examples, the predictive models described herein may be training prior to use and the training may continue with updated data sets that reflect additional information.

Figure 7:
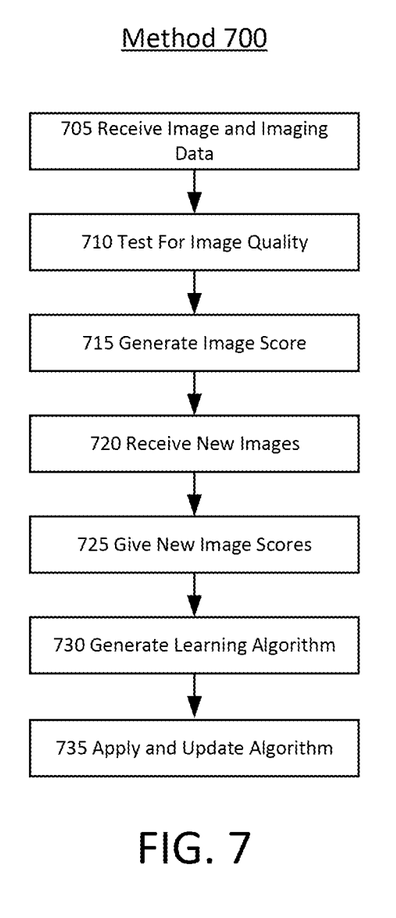
FIG. 7 is a flowchart of a method for applying predictive model according to an exemplary embodiment.

FIG. 7 is a flowchart illustrating a neural network according to an exemplary embodiment.

The method 700 can be performed with a probe, an administrator processor, a user device, a network, a server, and a data storage unit. It is understood that the method 700 and other methods or processes may be performed in a different order than described. The server can be one or more clouds or cloud servers including without limitation private clouds, public clouds, hybrid clouds, and multiclouds.

In action 705, one or more images can be received. The images and/or image data can be received by the administrator processor or user device from the probe. In other embodiments, the user device can receive the images from the probe or the administrator processor. The images can be transmitted over a wired or wireless network. As a nonlimiting example, the administrator processor can be connected with one or more wires to the probe. As another nonlimiting example, the administrator processor can receive the images over a wireless network from the probe. In other embodiments, the images can be received by a server over a wired or wireless network. The server can receive the data directly from the administrator processor, the probe, or the user device. In other embodiments, the images can be first sent to the data storage unit for short term or long-term storage. The images can include the sonographic or other visually oriented images captured by the probe or ultrasound transducer. The images can be received one-by-one or in a blended manner. The images can be blended and deblended at various stages of the method 700 to promote faster computation or training of the predictive model. Blending can mean combining two or more images together, and deblending can mean uncombining one image into two or more images. Similarly, the images can be compressed and decompressed at various points during the method 700. For example, the images can be compressed and sent to the server, at which point the images can be analyzed, after which the imagers can be decompressed and sent back to the administrator processor or user device. In some embodiments, the processor or administrator processor can transmit the one or more images to a data storage unit where the images can be stored for long term storage, later use, or later analysis. The data storage unit is discussed with further reference to FIG. 1.

In action 710, the quality of the images and/or image data can be tested. This action can be performed by the predictive model discussed with further reference to FIG. 5 and FIG. 6. The predictive model can be configured such that it tests the current image against one or more historical images retrieved from a data storage unit or server. The predictive model can be associated with the administrator processor, server, or user device and the processors located therein. In action 715, an image score can be generated. This action can be performed by the predictive model associated with the administrative processor, server, or user device and the processor located therein. The score can comprise any number of metrics. As a nonlimiting example, the score can range from a letter score such as A+ to F-, or from a numerical scale such as 10 to 0 or 100 to 0, or any numerical range. The score can also comprise other scales such as Very Good to Very Bad or other similar phraseology. The score can also comprise a relative or weighted grade, such that the current image and/or image data is compared with past or historical images. To generate the image score, the processor or predictive model can consider one of many nonlimiting factors: position of the probe, angle of the probe relative to the object; the pressure being applied by the probe on the object; image clarity; image dimension including width, length, and depth; one or more comparisons between the one or more images collected from the probes and one or more past or historical images. The past or historical images can include images from other patients, from the same patient, from other objects, from the same object, or from one or more specially generated images created to test the quality of other images.

In action 720 and 725, the processor can receive new images and generate new scores. These steps of receiving new images and generating score can be repeated any number of times. Based on any number of score generations, the processor can generate the predictive model in action 730. In action 735, the predictive model can be applied and updated any number of times with new parameters, images, image data, and scores.

Figure 8:
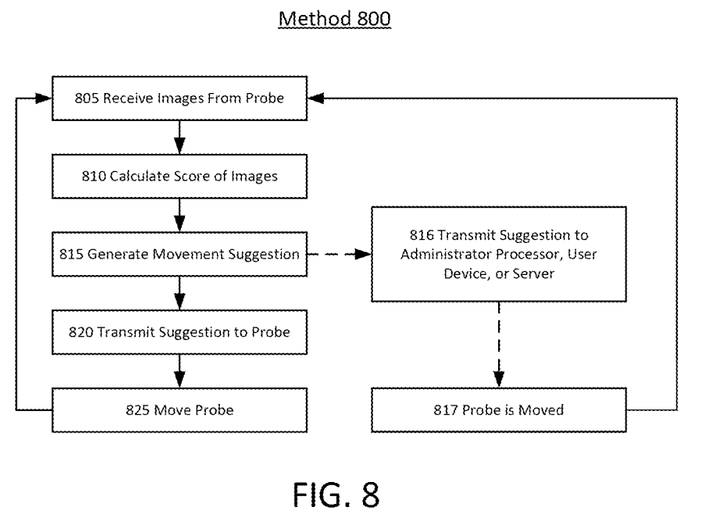
FIG. 8 is a flowchart of a method for using a predictive model to guide a probe according to an exemplary embodiment.

FIG. 8 is a flowchart illustrating a process for prompting an AI-controlled movable element on a probe. The process 800 can include a probe, an administrator processor, a user device, a server, a network, and a data storage unit.

In action 805, the images and/or image data are received from the probe. The probe is discussed with further reference to FIGS. 2-4. The images can be received by the administrator processor, the user device, or the server. The images can be transmitted over either a wired or wireless network. The images can include the sonographic or other visually oriented images captured by the probe or ultrasound transducer. The images can be received one-by-one or in a blended manner. The images can be blended and deblended at various stages of the method 800 to promote faster computation or training of the predictive model. Blending can mean combining two or more images together, and deblending can mean uncombining one image into two or more images. Similarly, the images can be compressed and decompressed at various points during the method 800. For example, the images can be compressed and sent to the server, at which point the images can be analyzed, after which the imagers can be decompressed and sent back to the administrator processor or user device.

In action 810, the predictive model generates or calculates a score of the images. The predictive model can be associated with the administrator processor, user device, or server. This action can be performed by the predictive model which can be configured to score the images and suggest a movement. The predictive model can be associated with the server, user device, or administrator processor. The predictive model is discussed with further reference to FIGS. 4-6. The score can comprise any number of metrics. In an exemplary embodiment, the predictive model is associated with the server. The generation or calculation of the image score is discussed with further reference to FIG. 7. As a nonlimiting example, the score can range from a letter score such as A+ to F−, or from a numerical scale such as 10 to 0 or 100 to 0, or any numerical range. The score can also comprise other scales such as Very Good to Very Bad or other similar phraseology. The score can also comprise a relative or weighted grade, such that the current image is compared with past or historical images or imaging data.

To generate the image score, the processor or predictive model can consider one of many nonlimiting factors: position of the probe, angle of the probe relative to the object; the pressure being applied by the probe on the object; image clarity; image dimension including width, length, and depth; one or more comparisons between the one or more images collected from the probes and one or more past or historical images. The past or historical images can include images from other patients, from the same patient, or from one or more specially generated images created to test the quality of other images. These examples can apply to any of the figures, not just FIG. 8.

In action 815, the predictive model can, upon generate a movement suggestion. A movement suggestion can include any haptic, visual, auditory, or mechanical suggestion. The haptic suggestion can be performed by the probe. As a nonlimiting example, the motor within the housing or handle can vibrate in a certain fashion to indicate a suggested movement to the right or left, forward or back, or a change in the rotation of the probe such as pitch or yaw. The visual suggestion can include one or more visual cues on the probe itself or on an accompanying visual display on the user device, administrator processor, or other computer-enabled device with a visual display. As a nonlimiting example, the probe can include one or more lights or LEDs on the exterior of the probe that can light up in the direction deemed the most helpful for creating a sufficiently good image. As another nonlimiting example, the visual display on the administrator processor, user device, or other computer-enabled device can visually alert the user of the probe to an area that needs to be rescanned or otherwise reengaged with the probe. For example, the screen may put an arrow next to a section of an ultrasound image that needs to be reengaged with the probe. In other embodiments, the mechanical suggestion can include a moving of the movable element in the direction that is suggested or commanded by the predictive model. In 820, the suggestion can be transmitted to the probe via a wired or wireless network. The suggestions can be transmitted by the administrator processor, the user device, or the server to the probe. In action 825, the probe can be moved via the movable element. The movable element is discussed with further reference to FIG. 2 and FIG. 3. This action can also be performed by the predictive model discussed with further reference to FIGS. 5-6. The movement suggestion can be a visual or haptic suggestion, or a movement of the movable element. For example, the predictive model can generate a transmit a visual cue to the user device or administrator processor, indicating to the user of the probe that the probe should be moved according to the prompt. As another nonlimiting example, the haptic suggestion can be transmitted from the processor to the probe. The haptic can include a vibration, indicating the probe is being positioned in either a correct or incorrect position. That is, the probe can be configured such that a vibration means either a good position or a bad position in terms of resulting image quality or image score. The processor can also generate a suggestion for the movable element itself. For example, the processor can generate and transmit a suggestion or command to the movable element such that movable element moves along a linear or rotational axis, thus positioning the lens a position that will produce a higher quality image or a higher image score according to the predictive model.

In some aspects, the techniques described herein relate to a probe with a movable element connecting a lens and a handle, the probe including: a body, wherein the body further includes: a handle; a lens; and a movable element connecting the handle and the lens, the movable element configured to move the lens in response to one or more commands from a predetermined algorithm configured to determine a movement of the lens in relation to an object.

In some aspects, the techniques described herein relate to a probe, wherein the probe is an ultrasound probe configured to generate one or images of the object.

In some aspects, the techniques described herein relate to a probe, wherein the movable element can move in three linear dimensions and three rotational dimensions.

In some aspects, the techniques described herein relate to a probe, wherein the handle houses a processor, one or more motor controllers, and one or more motors configured to move the movable element.

In some aspects, the techniques described herein relate to a probe, wherein the probe further includes a sensor configured to determine an orientation of the lens with respect to an object.

In some aspects, the techniques described herein relate to a probe, wherein the lens includes at least one selected from the group of a convex lens, linear lens, phased array lens, micro convex lens, T-type lens, biplanar lens, endocavitary lens, and intrarectal lens.

In some aspects, the techniques described herein relate to a probe, wherein the probe is further configured to be connected via a wired connection with an administrator processor configured to receive and analyze one or more images captured by the probe.

In some aspects, the techniques described herein relate to a system for generating an algorithm configured to acquire improved ultrasound images, the system including: a probe including: a body, wherein the body further includes: a handle; a lens; and a movable element connecting the handle and the lens, the movable element configured to move the lens in response to one or more commands from a predetermined algorithm configured to determine a movement of the lens in relation to an object; and a processor configured to move the movable element of the probe, wherein the processor is further configured to: receive, from the probe, one or more images; analyze, upon receiving the images, the images for quality; generate, upon analyzing the images for quality, a predictive model configured to determine an image score based on the quality of the one or more images wherein the predictive model includes a model of image quality versus the location of the probe with respect to the subject; calculate, by the predictive model, the image score for one or more images; and move, upon calculating the image score, the movable element of the probe.

In some aspects, the techniques described herein relate to a system, wherein predictive model is configured to: analyze one or more inputs, the inputs including a probe location, a probe angle, and the one or more images; and generate the image score based on the inputs.

In some aspects, the techniques described herein relate to a system, wherein the processor is further configured to store, upon receiving the images from the probe, the images in a data storage unit.

In some aspects, the techniques described herein relate to a system, wherein the system further includes a server.

In some aspects, the techniques described herein relate to a system, wherein the server is a cloud server.

In some aspects, the techniques described herein relate to a system, wherein the processor is configured to transmit the one or more images to the cloud server, whereupon the server can analyze the images for quality, whereupon the cloud server can transmit the score to the processor.

In some aspects, the techniques described herein relate to a system, wherein the system further includes a user device configured to display the one or more images received from the probe.

In some aspects, the techniques described herein relate to a system, wherein the processor is further configured to display on the user device where the lens should be placed on an object in order to obtain a higher image score.

In some aspects, the techniques described herein relate to a method for applying a probe guided by a predetermined algorithm, the method including the steps of: receiving, by a processor from a probe, one or more images; analyzing, by the processor upon receiving the images, the images for quality; generating, by the processor upon analyzing the images for quality, a predictive model configured to determine an image score based on the quality of the images wherein the predictive model includes a model of image quality versus a location of the probe with respect to an object; calculating, by the predictive model, the image score for the one or more images; and moving, by the processor upon calculating the image score, a movable element of the probe.

In some aspects, the techniques described herein relate to a method, wherein the steps further include transmitting, upon receiving the one or more images from the probe, the one or more images to a data storage unit configured to store the one or more images for long term storage.

In some aspects, the techniques described herein relate to a method, wherein the steps further include: transmitting, by the processor, the one or more images to a user device; and displaying, by the user device, where a lens associated with the probe should be placed on an object in order to obtain a higher image score.

In some aspects, the techniques described herein relate to a method, wherein the predictive model is associated with a neural network.

In some aspects, the techniques described herein relate to a method, wherein the movable element can be moved any number of times by the processor.

Although embodiments of the present invention have been described herein in the context of a particular implementation in a particular environment for a particular purpose, those skilled in the art will recognize that its usefulness is not limited thereto and that the embodiments of the present invention can be beneficially implemented in other related environments for similar purposes. The invention should therefore not be limited by the above-described embodiments, method, and examples, but by all embodiments within the scope and spirit of the invention as claimed.

The invention is not to be limited in terms of the particular embodiments described herein, which are intended as illustrations of various aspects. Many modifications and variations can be made without departing from its spirit and scope. Functionally equivalent systems, processes and apparatuses within the scope of the invention, in addition to those enumerated herein, may be apparent from the representative descriptions herein. Such modifications and variations are intended to fall within the scope of the appended claims. The invention is to be limited only by the terms of the appended claims, along with the full scope of equivalents to which such representative claims are entitled.

It is further noted that the systems and methods described herein may be tangibly embodied in one or more physical media, such as, but not limited to, a compact disc (CD), a digital versatile disc (DVD), a floppy disk, a hard drive, read only memory (ROM), random access memory (RAM), as well as other physical media capable of data storage. For example, data storage may include random access memory (RAM) and read only memory (ROM), which may be configured to access and store data and information and computer program instructions. Data storage may also include storage media or other suitable type of memory (e.g., such as, for example, RAM, ROM, programmable read-only memory (PROM), erasable programmable read-only memory (EPROM), electrically erasable programmable read-only memory (EEPROM), magnetic disks, optical disks, floppy disks, hard disks, removable cartridges, flash drives, any type of tangible and non-transitory storage medium), where the files that comprise an operating system, application programs including, for example, web browser application, email application and/or other applications, and data files may be stored. The data storage of the network-enabled computer systems may include electronic information, files, and documents stored in various ways, including, for example, a flat file, indexed file, hierarchical database, relational database, such as a database created and maintained with software from, for example, Oracle® Corporation, Microsoft® Excel file, Microsoft® Access file, a solid state storage device, which may include a flash array, a hybrid array, or a server-side product, enterprise storage, which may include online or cloud storage, or any other storage mechanism. Moreover, the figures illustrate various components (e.g., servers, computers, processors, etc.) separately. The functions described as being performed at various components may be performed at other components, and the various components may be combined or separated. Other modifications also may be made.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, to perform aspects of the present invention.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions specified herein. These computer-readable program instructions may also be stored in a computer-readable storage medium that can direct a computer, a programmable data processing apparatus, and/or other devices to function in a manner, such that the computer readable storage medium having instructions stored therein comprises an article of manufacture including instructions which implement aspects of the functions specified herein.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions specified herein.

GLOSSARY

Cloud: Cloud can mean, without limitation, one or more cloud servers, cloud processors, cloud systems, public clouds, private clouds, hybrid clouds, cloud computers, multi-clouds, or high-performance clouds.

What is claimed is:

1. A probe with a movable element connecting a lens and a handle, the probe comprising:
    a body, wherein the body further comprises:
        a handle configured to be held by one or more hands of a human user;
        a lens; and
        a movable element connecting the handle and the lens, the movable element configured to move the lens in response to one or more commands from a predetermined algorithm configured to determine a movement of the lens in relation to an object and wherein the lens moves independently of the handle while the handle remains still.

2. The probe of claim 1, wherein the probe is an ultrasound probe configured to generate one or images of the object.

3. The probe of claim 1, wherein the movable element can move in three linear dimensions and three rotational dimensions.

4. The probe of claim 1, wherein the handle houses a processor, one or more motor controllers, and one or more motors configured to move the movable element.

5. The probe of claim 1, wherein the probe further comprises a sensor configured to determine an orientation of the lens with respect to an object.

6. The probe of claim 1, wherein the lens comprises at least one selected from the group of a convex lens, linear lens, phased array lens, micro convex lens, T-type lens, biplanar lens, endocavitary lens, and intrarectal lens.

7. The probe of claim 1, wherein the probe is further configured to be connected via a wired connection with an administrator processor configured to receive and analyze one or more images captured by the probe.

8. A system for generating an algorithm configured to acquire improved ultrasound images, the system comprising:
    a probe comprising:
        a body, wherein the body further comprises:
            a handle configured to be held by one or more hands of a human user;

a lens; and a movable element connecting the handle and the lens, the movable element configured to move the lens in response to one or more commands from a predetermined algorithm configured to determine a movement of the lens in relation to an object, and wherein the lens moves independently of the handle while the handle remains still; and a processor configured to move the movable element of the probe, wherein the processor is further configured to:

receive, from the probe, one or more images;

analyze, upon receiving the one or more images, the one or more images for quality;

generate, upon analyzing the one or more images for quality, a predictive model configured to determine an image score based on the quality of the one or more images wherein the predictive model comprises a model of image quality versus the location of the probe with respect to the subject;

calculate, by the predictive model, the image score for the one or more images; and move, upon calculating the image score, the movable element of the probe.

9. The system of claim 8, wherein the predictive model is configured to:

analyze one or more inputs, the inputs comprising a probe location, a probe angle, and the one or more images; and generate the image score based on the inputs.

10. The system of claim 8, wherein the processor is further configured to store, upon receiving the one or more images from the probe, the one or more images in a data storage unit.

11. The system of claim 8, wherein the system further comprises a server.

12. The system of claim 11, wherein the server is a cloud server.

13. The system of claim 12, wherein the processor is configured to transmit the one or more images to the cloud server, whereupon the server can analyze the one or more images for quality, whereupon the cloud server can transmit the score to the processor.

14. The system of claim 8, wherein the system further comprises a user device configured to display the one or more images received from the probe.

15. The system of claim 14, wherein the processor is further configured to display on the user device where the lens should be placed on an object in order to obtain a higher image score.

16. A method for applying a probe guided by a predetermined algorithm, the method comprising the steps of:

providing a probe comprising a body, wherein the body further comprises:

a handle configured to held by one or more hands of a human user;

a lens; and a movable element connecting the handle and the lens, the movable element configured to move the lens and wherein the lens moves independently of the handle while the handle remains still;

receiving, by a processor from the probe, one or more images;

analyzing, by the processor upon receiving the images, the images for quality;

generating, by the processor upon analyzing the images for quality, a predictive model configured to determine an image score based on the quality of the one or more images wherein the predictive model comprises a model of image quality versus a location of the probe with respect to an object;

calculating, by the predictive model, the image score for the one or more images; and moving, by the processor, upon calculating the image score, a movable element of the probe.

17. The method of claim 16, wherein the steps further comprise transmitting, upon receiving the one or more images from the probe, the one or more images to a data storage unit configured to store the one or more images for long term storage.

18. The method of claim 16, wherein the steps further comprise:

transmitting, by the processor, the one or more images to a user device; and displaying, by the user device, where a lens associated with the probe should be placed on an object in order to obtain a higher image score.

19. The method of claim 16, wherein the predictive model is associated with a neural network.

20. The method of claim 16, wherein the movable element can be moved any number of times by the processor.

* * * * *